United States Patent
Kumar et al.

(10) Patent No.: US 6,323,394 B1
(45) Date of Patent: Nov. 27, 2001

(54) TISSUE CULTURE PROCESS FOR PRODUCING A LARGE NUMBER OF VIABLE MINT PLANTS IN VITRO

(75) Inventors: Sushil Kumar; Shiv Kumar Gupta; Savithri Bhat; Rakesh Tuli, all of Lucknow (IN)

(73) Assignee: Council of Scientific & Industrial Research, New Dehli (IN)

( * ) Notice: Subject to any disclaimer, the term of this patent is extended or adjusted under 35 U.S.C. 154(b) by 0 days.

(21) Appl. No.: 09/263,485

(22) Filed: Mar. 8, 1999

Related U.S. Application Data

(63) Continuation-in-part of application No. 08/792,545, filed on Jan. 31, 1997, now Pat. No. 5,898,001.

(51) Int. Cl.⁷ .............................. A01H 1/00; C12N 15/82
(52) U.S. Cl. ...................... 800/278; 435/468; 435/469; 435/470; 800/293; 800/294
(58) Field of Search ........................... 800/278; 435/468, 435/440

(56) References Cited

PUBLICATIONS

Niu, X. et al. "Factors Affecting Agrobacterium tumefaciens–mediated transformation of peppermint" Plant Cell Raports 19(3) pp. 304–310 Jan. 1999.*
Diemer, F. et al. "Agrobacterium tumefaciens mediated transformation of Mentha spicata and mentha arvensis" Plant Cell Tissue and Organ Culture 57 (1) pp. 75–78 1999.*
Diemer, F. et al. "High efficiency transformation of peppermint (mentha x piperita I.) with *Agrobacterium tumefaciens*" Plant Science 136(1) pp. 101–108 Aug. 7, 1998.*

\* cited by examiner

*Primary Examiner*—Bruce R. Campell
(74) *Attorney, Agent, or Firm*—Birch, Stewart, Kolasch & Birch, LLP

(57) ABSTRACT

The present invention relates to a tissue culture process for producing a large number of genetically transformed viable mint plants in vitro. The process of the present invention employs specified pieces of an internodal segment of the stem of the mint plant as the starting material and identifies medium, culture and transformation conditions for producing a large number of genetically transformed plants. Such plants can be selected for desirable characteristics.

31 Claims, No Drawings

TISSUE CULTURE PROCESS FOR PRODUCING A LARGE NUMBER OF VIABLE MINT PLANTS IN VITRO

This application is a continuation-in-part of Ser. No. 08/792,545 filed on Jan. 31, 1997, now U.S. Pat. No. 5,898,001 the entire contents of which are hereby incorporated by reference.

FIELD OF THE INVENTION

The present invention relates to a tissue culture process for producing a large number of viable mint plants in vitro. The process of the present invention employs specified pieces of stem of the mint plant as the starting material and identifies media and culture conditions for producing a large number of plants. Such plants can be used for micropropagation, selection of mutants, production of plants with altered levels of endogenous secondary metabolites and for genetic engineering.

BACKGROUND OF THE INVENTION

Various species of mint plants are grown primarily in India, China and Japan commercially for mint oil, menthol, vitamins and other metabolites that are valuable to the pharmaceutical industry. These are used in aromatic oils and herbal medicines. The present invention deals with a tissue culture process for the development of a large number of plants from a specified part of mint plant. The process of the present invention opens up new possibilities for producing somaclonal and physiological variants and for genetic improvement of mints by modern techniques of agrobiotechnology.

Mints are of interest globally because of their valuable secondary metabolites, especially mint oils and menthol for the industry. Since it is a vegetatively propagated crop, mutation techniques have largely been applied to improving characteristics like disease resistance, yield, metabolites and oil content. However, it is possible to apply tissue culture techniques for the improvement of mints by the selection of somaclonal variants and genetic engineering. The main objective of the present invention is to provide a simple process for large scale tissue culture based micropropagation of mints. Another objective of the present invention is to provide a powerful tool for the isolation of physiological variants, somaclones and mutants and for genetic manipulation of mints.

Plant regeneration by tissue culture techniques is well established. A wide varied of plant species has been successfully regenerated in vitro via organogenesis or somatic embryogenesis. Organogenesis leads to organ formation i.e. shoot (or root), which can be isolated to induce development of roots (or shoots) to produce full plants while somatic embryogenesis leads to the development of somatic embryos (embryos developed without genetic fertilization) which have both shoot and root initially and are capable of developing into whole plants. Although the ability of individual parts of plants and cells to regenerate into complete plants (called totipotency) is a well known phenomenon, each plant or plant part requires specialized studies to invent the conditions that allow such regeneration. Some of the factors controlling growth and differentiation of such cultures have been determined. The establishment of interactions among different groups of phytohormones, and growth regulators alone or in combinations are responsible for certain inter-relations existing among cells, tissues and organs. So there seems to be a consensus that the success in inducing differentiation depends upon the type of plant part ("explant"), the physiological condition of the explant and physical and chemical milieu of explant during culture. Due to this, the science of tissue culture has been directed to optimize the physiological conditions of source plant, the type of explant, the culture conditions and the phytohormones used to initiate tissue culture. This substantiates the fact that development of a new process for proliferation of plants by tissue culture is not obvious.

One major aspect that has to be investigated on a case-by-case basis is the type of plant growth regulators and the amount of plant growth regulators that induce regeneration. Besides, chemical composition of the medium, temperature and other culture conditions play an important role in the induction of organogensis and somatic embryogenesis and their maturation to healthy fertile plants thereof. The response to medium, hormones and growth conditions differs from plant species to species and variety to variety. Thus inventing conditions for efficient regeneration of plants requires developing specialized knowledge about a given plant.

Another major area where innovativeness is required in tissue culture, is identifying the plant part that efficiently responds to the culture conditions and leads to prolific regeneration. Not all plant parts of a given species are amenable to efficient regeneration. It is a complex combination of the explant selected identified for regeneration, physiological state of the explant, growth conditions and growth regulators that determines success of a plant in tissue culture. Different explants from a given plant usually show entirely different and often unpredictable response to growth conditions for proliferation. No general principles can be applied to achieve regeneration. In each case, identification of the explant and identification of the culture conditions are innovative steps in the development of a tissue culture method for regeneration of a plant part into a number of plants.

To date, regeneration of many species and cultivars of Mentha has been reported through tissue culture. But the processes described earlier are not very efficient. The starting materials (explant) used in the earlier processes were different. For example, these processes utilized axillary buds, leaf pieces and embryos as the starting material. In this respect several reports on tissue culture of mints have been published. Some of these are also related to the establishment of cell suspension cultures and callus, and are listed below for convenience and reference. Application of tissue culture techniques for the production and biosynthesis of useful plant constituents has been exploited for the production of alkaloids from excised root culture, callus and by crown gall tissue in a number of plants. (West F R, Jr and Mike E S 1957. Synthesis of atropine by isolated roots and root callus cultures of ballandona, Botan.Gaz. 119:50–54; Klein R M 1960, Plant tissue culture: a possible source of plant constituents, Econ. Botany 14: 286–289 ). Cell suspension and callus cultures of *Mentha piperita* & *M. spicata* were reported to enable the production and biosynthesis of secondary metabolites (Lin and Staba 1961, Peppermint and spearmint tissue cultures, callus formation and submerged culture, Leoydia 24: 139–145; Wang and Staba 1963, Peppermint and spearmint Tissue culture II: Dual-Carboy culture of spearmint Tissue. Jour. of Pharmaceutical Science 52:1058–1062). Such cell suspensions were later reported to biotransform certain precursors into monoterpenes (Aviv D and Gulan E 1978, Biotransformation of monoterpenes by Mentha cell lines: Conversion of pulegone to isomenthone. Planta Medica 33;70–77; Aviv D, Krochmal E, Dantes A and Gulan E. 1983, Biotransformation of monoterpene by Mentha cell lines conversion of pulegone-substituents and related unsaturated α-β ketones. Planta Medica 47:7–10). Triterpenes were reported to be produced by callus tissue of *Mentha arvensis* (Karasawa D and Shimzu S 1980, Triterpene acids in callus tissue from *Mentha arvensis* var. Piperascens.Mol.Agric.Biol Chem.44: 1203–1205). Small quantities of menthol were also detected in suspension cultures and callus cultures with the help of GLC TLC. (Bhaumik C and Dutta P C 1982, Menthol in static and suspension cultures of *Mentha arvensis* Lin: var piperascens Holmes: Indian Drugs (July) 387–388). These reports did not aim at the regeneration of plants from the above said cultures.

Multiplication of shoots from axillary buds of Mentha spp was reported by tissue culture techniques (Rech E L and Pires M J P 1986. Tissue culture propagation of Mentha spp. by the use of axillary buds. Plant Cell Reports 5:17–18, Revishankar G A and Venkatraman L V 1988. Rapid multiplication of plants from cultured auxillary buds of *Mentha piperita*. Philippine Jour. of Science 117:121–129). These reports deal with the multiplication of shoots from pre-existing meristems in axis of leaves, and up to 15 shoots could be obtained from single explant of *M.viridis, M.pulegium* and *M.piperita* which are reported as highly responding species for tissue culture. In the case of recalcitrant mints, like *Mentha arvensis*, a few shoots were obtained.

Regeneration of shoots was also reported from leaf explants for *M. piperita* and *M. spicata* again, the species known to respond well to tissue culture (Repcakoa K Rychlova G Cellorova B and Honcariv R 1986, Micropropagation of *Mentha piperita L.* through tissue cultures Herba Hungarica, Tom 25:77–88; Van Eck J M & Kitto S L 1992, Regeneration of peppermint and orangemint from leaf disc. Plant Cell Tiss.Org. Cult. 30:41–49). These leaf based protocols, however are not efficiently reproducible and produce only a few shoots per explant.

Regeneration of shoots from callus cultures of *Mentha piperita* and *M.spicata* has also been reported. In these cases, the callus was developed either from mature or immature embryos obtained from developed or developing seeds respectively. Although differentiation of shoots from callus was observed, the efficiency was extremely low and only 5 plants could be regenerated from two out of 65 calli. The explant used in this report i.e. seeds are in paucity because mints are propagated vegetatively (Van Eck J M and Kitto S L 1990, Callus initiation and regeneration in Mentha. Hort. Science 25: 804–806) suggesting that the number of shoots obtained and the success rate is poorer than when explants containing pre-existing meristems were used. Regeneration of *M. piperita L.* from protoplasts was also reported. The regeneration from protoplasts involves the formation of single isolated cells that multiply to give callus and then differentiate to give shoots. However, the regeneration efficiency was very poor (Sato H, Enomoto S. Oka S, Hosomi K and Ito Y 1993, Plant regeneration from protoplasts of peppermint *mentha piperita L*. Plant Cell Rep. 12: 546–550; Sato H, Enomoto S. Oka S, Hosomi K, Ito Y, 1994, the effect of 4-1-phenyl N(4 pyridyl) urea on protoplast culture of peppermint *Mentha piperita L*. Plant Tissue Culture Lett. 11: 134–138). The technique for the regeneration of plants from protoplasts was recently applied to develop interspecific somatic hybrids between peppermint and gingermint by protoplast fusion through electrofusion. The hybrid was confirmed by analysis of oil content, chromosome number and RAPD based DNA analysis (Sato H, Yamada K, Mii M, Hosomo K, Okuyama S, Uzawa M, Ishikawa H, Ito Y, 1996: Production of interspecific somatic hybrid between peppermint and gingermints, Plant Science 115, 101–102).

Wild strains of the bacterium *Agrobacterium tumefaciens* have been reported to develop crown gall or shooty teratomas on stem of *M.piperita*. Octopine and succinamopine type T-DNA containing Agrobacterium developed crown galls while nopaline type T-DNA containing Agrobacterium developed shooty teratomas. No attempts were made in these cases to get normal mature plants from such teratomas (Spencer A, Hamill, John D and Rhodes Micheal J C 1990, Production of terpenes by differentiated shoot culture of *Mentha citrata* transformed with *Agrobacterium tumefaciens* T37. Plant Cell Rep 8: 601–604).

Table 1 summarizes the state of art of tissue culture processes related to mint plant as covered by patents or described in literature. It is then followed by statement describing the process invented by us in contrast to the known state of art.

TABLE 1

State of art of tissue culture work on Mentha

| Report | Mode of regeneration | Phytohormones | Explant | Remarks |
|---|---|---|---|---|
| 1. Lin & Staba, 1961 Peppermint and spearmint tissue cultures, callus formation and submerged culture, Leoydia 24:139–145 | Callus cultures & submerged culture | BTOA, 2, 4-D, coconut water | Stem & seeds | Culture of stem of peppermint & spearmint on medium formed shoot buds and roots at the nodes where preexisting meristems are available. Culture of stem on auxins (BTOA and 2, 4D) containing medium gave callus which could not be regenerated into plants. |
| 2. Wang and Staba 1963, Peppermint and Spearmint Tissue Culture II: dual Carboy culture of Spearmint Tissue. Journal of Pharmaceutical Science 52:1058–1062 | Suspension cultures | 2, 4-D | Stem | Characterisation of spearmint (*Mentha Spicata*) cell inoculated in carboys receiving constant air flow and agitation. The effect of certain antifoam and antibiotic compounds on spearmint tissue growth are discussed. Report does not show regeneration of plants. |
| 3. Aviv D and Galun E. 1978, Biotransformation of | Suspension culture | nil | Cells | Report indicates that cell lines derived from |

TABLE 1-continued

State of art of tissue culture work on Mentha

| Report | Mode of regeneration | Phytohormones | Explant | Remarks |
| --- | --- | --- | --- | --- |
| monoterpenes by Mentha cell lines conversion of pulegone to isomenthone planta medica 33: 70–77 | | | | different Mentha chemotypes were capable to biotransform pulegone to isomenthone. No regeneration of plants. |
| 4. Aviv D, Krochmal E, Dentes A, and Galun E. 1983. Biotransformation of monoterpenes by Mentha cell lines: conversion of pulegone substituents and related unsaturated α-β ketones Planta, Medica 47:7–10 | Suspension culture | nil | Cells | In this report the biotransformation of certain compounds with similarities to pulegone is discussed. No regeneration of plants. |
| 5. Karasawa D and Shimizu S. 1980, Triterpene Acids in callus tissues from *Mentha arvensis* var *piperascens* Mol. Agric. Biol. chem. 44:1203–1205. | Callus | NAA & Kin | Stem | Describes the effect of NAA and kinetin in media on the composition of triterpenes in the callus tissue of *Mentha arvensis* var *piperascens* (Japanese mint) & comparison between callus tissue and original plants. Does not show regeneration of plants. |
| 6. Bhaumik C and Dutta P C 1982, Menthol in static and suspension cultures of *Mentha arvensis* Lin var pipersens Holmes: Indian Drug (July) 387–388 | Callus suspension | 2, 4-D, Kin | Young leaf | Four months old callus and isolated cells (fresh) including the medium yielded menthol which was identified by TLC & GLC techniques. Does not show regeneration of plants. |
| 7. Rech E L and Pires M J P 1986. Tissue culture propagation of Mentha spp. by the use of axillary buds Plant Cell Reports 5:17–18 | Regeneration of Mentha spp. by multiplication of axillary buds | BAP, Kin | Nodal segments | A method for rapid multiplication of Mentha spp. from nodal explant is discussed. Shoots produced from preexisting meristems. Process does not work for *Mentha arvensis* efficiently. |
| 8. Ravishankar G A and Venkataraman L V 1988. Rapid multiplication of plants from cultured axillary buds of *Mentha piperita* Phillippine Jour of Science 117:121–129 | Multiplication of axillary buds & regeneration of plants | 1AA, 2, 4D, NAA, IBA, Kin | Nodal segments | Describes the multiplication of shoots via inducing preexisting meristem in nodal tissue. Only 4 shoots per node were produced by this method for *M. pipereta*. This report does not work for *M. arvensis*. |
| 9. Repcakoa K. Rychlova M, Cellorova E and Honceriv R 1986, Micropropagation of *Mentha piperita* L. Through tissue cultures. Herba Hungarica, Tom 25:7288 | Regeneration of *Mentha piperita* | BAP, Kin | Immature leaf | Process of regeneration was not good because identification of the regenerative explant is not easy. |
| 10. Van Eck J M and Kitto S L 1992, Regeneration of pippermint and orange mint from leaf. Plant Cell Tissue Organ Culture 30:41–49 | Regeneration of Mentha plants via organogenesis | Coconut water BAP, NAA, TFBA | Leaf discs | Efficiency of shoot formation is very poor. Only a few shoots can be developed from one leaf with lower frequency. |
| 11. Van Eck J M & Kitto S L 1990, callus initiation and regeneration in Mentha. Hort. Science 25:804–806 | Callus initiation and regeneration of Mentha plant | NAA, BAP | Mature and immature embryos | Regeneration from callus raised from mature or immature embryo was obtained but differentiation of shoots from callus was very poor. Only 5 plants could be regenerated. Further, the explant i.e. mature or immature embryos is very rare because Mentha is vegetatively propagated crop. |
| 12. Sato H, Enomoto S, Oka S, Hosomi K and Ito Y, 1993, Plant Regeneration from protoplast of peppermint *Mentha piperita* L. Plant Cell Rep. 12:546–550 | Isolation & culture of protoplast for development of mature Mentha plant | BAP, NAA | Protoplast isolated from mesophyll cells of *Mentha piperita* leaves | Isolated protoplasts were demonstrated to induce cell division followed by callus formation & development of mature plant. But the technique is tricky, tedious & time consuming & cannot be adopted for commercial micropropagation |
| 13. Sato H, Enomoto S. Oka S, Hosomi K, Ito Y. 1994. The effect of 4-1-phenyl N (4 pyridyl) urea on protoplasts culture of peppermint *Mentha piperita* L. | Isolation & culture of protoplasts for development of mature Mentha | 4-PU, BAP, NAA, Kin and zeatin | Protoplast isolated from mesophyll cells of peppermint leaves | Isolated protoplasts were demonstrated to give calli & then regeneration of whole plant of *Mentha piperita*. But the technique of |

TABLE 1-continued

State of art of tissue culture work on Mentha

| Report | Mode of regeneration | Phytohormones | Explant | Remarks |
| --- | --- | --- | --- | --- |
| Plant Tissue Cul. Lett. 11:134–138 | plants | | | protoplast isolation & culture is very tricky, tedious & time consuming and not applicable for commercial micropropagation. |
| 14. Sato H, Yamada K, Mii M, Hosomi K, Okuyama S, Ozawa M, Ishikawa H, Ito Y. 4, 1996: Production of interspecific somatic hybrid between peppermint and gingermints. Plant Science 115, 101–102 | Protoplast fusion & regeneration of hybrid plants | 4PU & BAP and NAA | Protoplast of mesophyll cells from peppermint and gingermint leaves | Isolated protoplasts of peppermint & gingermint were fused by electrofusion method and hybrid was developed by regenerating plants from fused protoplast. The hybrid was confirmed by analysis of oil content, chromosome number and RAPD based DNA analysis |
| 15. Spencer A, Hamill, John D and Rhodes Michael J (1990, Production of terpenes by differentiated shoot culture of *Mentha citrata* transformed with *Agrobacterium tumefaciens* T37. Plant Cell Rep. 8:601–604. | Genetic transformation and culture of shoots | — | Internodal stem | Wild strain of the bacterium *Agrobacterium tumefaciens* have been reported to develop crown gall or shooty teratomas on stem of *M. piperita*. Octopine and succinamopine type T-DNA containing *Agrobacterium* developed crown galls while nopaline type T-DNA containing Agrobacterium developed shooty teratomas. |

Novelties in the Present Invention vis a vis State of Art

The present invention provides for the first time an efficient process for callus mediated organogenesis from an easily obtainable explant of mint plant, giving a large number of mature plants. This is potentially very useful in plant biotechnology for micropropagation, selecting variants and genetic transformation. Further, the invention also provides an improved process for exchange and conservation of disease free mint germplasm. The process of this invention is very simple and is applicable to a wide range of varieties and species of genus Mentha. The process also provides a simple method to alter the composition of essential oil in Mentha plants.

The process of the present invention employs the internodal region (for obtaining fully developed plants) as a starting material (explant), which is different from all the earlier reports (as given in Table 1). The process of the present invention for inducing a high frequency of de novo regenerants leads to whole plant development where the de nova regenerants are from tissues other than preexisting meristems. We could identify an explant that when cultured in suitable medium in the presence of certain combinations of commonly used growth regulators can stimulate a high frequency of differentiation of regenerants. Unlike reports 7 and 8 in Table 1, our process gives a larger number of shoots for all species of Mentha tested. Report 8 in Table 1 gives particularly poor regeneration from *Mentha arvensis* which is not the case with our process. Unlike reports 9 and 11 in Table 1, the internodal explant used by us is very convenient to obtain.

Earlier art dealing with multiple shoot formation used nodal tissue as the explant which consists of preexisting meristematic tissues in the form of axillary buds. The pre-existing meristematic tissue in such explants, when cultured in the presence of growth regulators starts growing to give a few shoots. The present invention uses internodal explant that does not contain preexisting primordia. The internodal explant gives a large number of shoots when cultured in medium supplemented with sufficient amount of growth regulators. The internodal segment has not been used in any earlier report for the regeneration of plants. Only report 15 given in Table 1 used internodal segment but that was for obtaining teratomas and not normal plants.

The phytohormone combinations and the explants used in the present invention are quite different from those used in any of the reports described in Table 1. The multiple shoot regeneration in our protocol was successful within certain limits of the phytohormone levels. For example, BAP functions efficiently at concentration of 8.88, $\mu$M to 88.8 $\mu$M with naphthalene acetic acid at 0.54 $\mu$M to 5.4 $\mu$M. $\gamma$, $\gamma$, dimethyl allyl amino purine works at 9.84 $\mu$M to 78.4 $\mu$M with naphthalene acetic acid 0.54 $\mu$M to 5.4 $\mu$M, and kinetin works at 9.29 $\mu$M to 69.3 $\mu$M with naphthalene acetic acid 0.54 $\mu$M to 5.4 $\mu$M. As described in Table 1 these ranges and combinations of phytohormone have not been used earlier for the development of a process for multiple shoot regeneration in mints.

OBJECTS AND DETAILED DESCRIPTION OF THE INVENTION

The present invention provided for the first time, an efficient process for callus mediated organogenesis and/or somatic embryogenesis from an easily obtainable explant of Mint plant to give a large number of mature plants. This method is potentially very useful in plant biotechnology for micropropagation, selection of variants & genetic transformation based upon infection by Agrobacterium or via bombardment of DNA coated microparticles.

Therefore the main object of the present invention is to provide a simple and reproducible tissue culture process for regeneration of a large number of mint plants from their explants (internode) which obviates the drawbacks in the processes reported earlier as detailed above.

Another object of the present invention is to provide an improved process for the exchange and conservation of disease free mint germplasm and to provide a large number of mint plants from their explants.

To meet the above objects, the applicants now provide a method of regenerating a large number of viable and fertile mint plants by tissue culture technique starting from a small tissue(explant) of mint plant, said method comprising:

i) cutting the internodal segment (explant) of mint plants,
ii) removing any contaminants such as fungus, bacteria, microbes etc. which are potentially harmful to the process, from the surface of the internodal segments (explants),
iii) culturing the decontaminated internodal segments from step (ii) in first medium capable of producing an organogenic callus, said first medium consisting of:
   a) Salts of any conventional medium,
   b) Vitamins of any conventional medium,
   c) Carbon source,
   d) Phytohormones (plant growth regulators), and
   e) Gelling agent,
at a pH in the range of 5.4 to 6.2 and sterilizing the medium by autoclaving. The culturing was effected at the temperature 20–35° C. in the presence of cool white light,
iv) continuing the culture of the said internodal segments until some callus along with several proliferating shoots are formed,
v) harvesting the shoots formed,
vi) culturing the shoots obtained from step (v) in second medium capable of inducing roots, said second medium comprising:
   a) Salts of any conventional medium,
   b) Vitamins of any conventional medium,
   c) Carbon source,
   d) Phytohormones (plant growth regulators), and
   e) Gelling agent,
at a pH in the range of 5.4 to 6.2 and sterilizing the medium by autoclaving, the culturing was effected at the temperature 20–35° C. in the presence of cool white light for a minimum period of two weeks to generate roots.

In the present invention the internodal segments employed are those obtained from plants grown in the field or those grown by the tissue culture in the laboratory. The internode used from the mint plants grown in the field are treated by conventional methods to remove the contaminants.

The first and second medium employed in the invention comprising salts of Murashige and Skoog (MS) medium, vitamins of B5 medium, carbon source and gelling agent. The preferred MS medium comprise the following salts:

| Component | concentration (mg/L) |
|---|---|
| Salts of MS medium: | |
| $NH_4NO_3$ | 1650 |
| $KNO_3$ | 1900 |
| $MgSO_4.7H_2O$ | 370 |
| $MgSO_4.H_2O$ | 169 |
| $ZnSO_4 7.H_2O$ | 8.6 |
| $CuSO_4.5H_2O$ | 0.025 |
| $CaCl_2.2H_2O$ | 440 |
| KI | 83 |
| $CoCL_2.2H_2O$ | 0.025 |
| $KH_2PO_4$ | 170 |
| $H_3BO_3$ | 6.2 |
| $Na_2MoO_4.2H_2O$ | 0.25 |
| $FeSO_4.7H_2O$ | 27.85 |
| $Na_2EDTA$ | 37.3 |
| Myoinositol | 100. |

Further, the preferred vitamins used in the first and second medium are:

| Content | concentration (mg/L) |
|---|---|
| Nicotinic acid | 1.0 |
| Pyridoxine HCl | 1.0 |
| Thiamine HCl | 10.0 |

In addition, the preferred carbon source used in the first and the second medium is selected from sucrose or glucose and is employed at a range of 1 to 6% w/v.

The phytohormones employed in the first medium are selected from cytokinins, auxins or cytokinin active urea or a combination thereof. More specifically, the auxin employed is selected from the group consisting of indole acetic acid, indole butyric acid, and naphthalene acetic acid at a concentration range varying between 0.1 to 10 $\mu$M, and the cytokinins employed in the first medium is selected from a group consisting of 6-benzylaminopurine, $\gamma$ $\gamma$ dimethyl allyl aminopurine and kinetin at a concentration range varying between 5 to 90 $\mu$M. The cytokinin urea employed in the first medium is selected from the group consisting of diphenyl urea, 4-1-phenyl N (N-pyridyl) urea at a concentration range varying between 1 to 20 $\mu$M.

On the other hand, the preferred phytohormones employed in the second medium are selected from auxins such as indole acetic acid, indole butyric acid and naphthalene acetic acid at a concentration of up to 50 $\mu$M.

The decontamination of the explant is effected by dipping in a solution containing at least one sterilizing agent selected from the group consisting of sodium hypochlorite, calcium hypochlorite, mercuric chloride, ethyl alcohol etc.

The gelling agent used is selected from agar, GELRITE™ (phytagel) or any gelling agent at a concentration range 0.2 to 1.2% w/v.

The concentration of salts of the MS medium mentioned in steps (iii) and (vi) was used in full quantities mentioned above or at half the level on weight by volume basis. The shoots regenerated by the said tissue culture process can be used for micropropagation of mint plants. The regenerated shoots contain altered/unaltered levels of secondary metabolites depending on phytohormone combinations used in the medium. The mint plants developed from the regenerated shoots of the present invention contain altered/unaltered levels of secondary metabolites useful for industrial application. The organogenic callus and the regenerated shoots can be used for genetic transformation based on infection by Argrobacterium or via bombardment of DNA coated microparticles. The shoots regenerated by the present tissue culture process can be used for production of disease-free mint plants or these can be effectively used for the exchange and conservation of disease-free mint germplasm.

The most preferred process of the present invention comprises:

i) cutting the internodal segment (explant) of mint plants,
ii) removing any contaminants such as fungus, bacteria, microbes etc which are potentially harmful to the process, from the surface of the internodal segments (explants),
iii) culturing the decontaminated internodal segments from step (ii) in a medium given in Table. 2

TABLE 2

| Component | Concentration (mg/L) |
|---|---|
| A. Salts of MS medium: | |
| NH$_4$NO$_3$ | 1650 |
| KNO$_3$ | 1900 |
| MgSO$_4$.7H$_2$O | 370 |
| MgSO$_4$H$_2$O | 169 |
| ZnSO$_4$.7H$_2$O | 8.6 |
| CuSO$_4$.5H$_2$O | 0.025 |
| CaCl$_2$.2H$_2$O | 440 |
| KI | 83 |
| CoCl$_2$2H$_2$O | 0.025 |
| KH$_2$PO$_4$ | 170 |
| H$_3$BO$_3$ | 6.2 |
| Na$_2$MoO$_4$.2H$_2$O | 0.25 |
| FeSO$_4$.7H$_2$O | 27.85 |
| Na$_2$EDTA | 37.3 |
| Myoinositol | 100 |
| B. Vitamins of B5 medium | |
| Nicotinic acid | 1.0 |
| Pyridoxine HCl | 1.0 |
| Thiamine HCl | 10.0 |
| Carbon source: | |
| Sucrose /Glucose | 30000.0 |
| D. Hormones (growth regulators) | |
| Cytokinins | 1 to 100 μM |
| Auxins | 0.1 to 10 μM |
| E. Gelling Agents | 0.2 to 1.2% w/v | at a pH in the range of 5.4 to 6.2. sterilising the medium by autoclaving, and the culturing being effected at a temperature in the range of 20–35° C. in the presence of cool white light, iv) continuing the culture of said internodal segments until some callus along with several proliferating shoots are formed, v) harvesting the shoots formed, vi) culturing the shoots in a medium employed for the formation of roots as given in Table 3.

TABLE 3

| Component | concentration (mg/L) |
|---|---|
| A. Salts of MS medium: | |
| NH$_4$NO$_3$ | 1650 |
| KNO$_3$ | 1900 |
| MgSO$_4$.7H$_2$O | 370 |
| MnSO$_4$H$_2$O | 169 |
| ZnSO$_4$.7H$_2$O | 8.6 |
| CuSO$_4$.5H$_2$O | 0.025 |
| CaCl$_2$.2H$_2$O | 440 |
| KI | 83 |
| CoCl$_2$.2H$_2$O | 0.025 |
| KH$_2$PO$_4$ | 170 |
| H$_3$BO$_3$ | 6.2 |
| Na$_2$MoO$_4$.2H$_2$O | 0.25 |
| FeSO$_4$.7H$_2$O | 27.85 |
| Na$_2$EDTA | 37.3 |
| Myoinositol | 100 |
| B. vitamins of B5 medium: | |
| Nicotinic acid | 1.0 |
| Pyridoxine HCl | 1.0 |
| Thiamine HCl | 10.0 |
| C. Carbon source | |
| Sucrose/Glucose | 30000.0 |

TABLE 3-continued

| Component | concentration (mg/L) |
|---|---|
| D. Hormones (growth regulators) | |
| Auxins | up to 50 μM |
| E. Gelling Agents | 0.2 to 1.2% w/v | at a pH in the range of 5.4 to 6.2 and sterilising the medium by autoclaving, effecting the culturing at a temperature in the range of 20–35° C. The plantlets so formed, if desired, according to requirements, can be transferred to the soil for growing mint plants on a very large scale.

According to another feature of the invention, the internode segments employed may be those obtained from the plants grown in the fields or those grown by tissue culture in the laboratory. Particularly in the case of internodes used from the plants grown in the fields, it is essential to treat them to remove the contaminants. This treatment can be made by any conventional methods which include treatment with hypochlorites, mercuric chloride, ethyl alcohol etc.

The hormones (growth regulators) employed in the culture medium may be selected from cytokinins such as BAP(6 benzyl amino purine or 6-benzyl adenine), zeatin, 2iP (γ, γ dimethyl allylamnino purine ), kinetin; auxins such as IAA (indole acetic acid), NAA (naphthalene acetic acid ), IBA (indole butyric acid) and cytokinin active urea such as TDZ (1-phenyl-3, 1,2,3 thidiazol-5-yl urea), DU (diphenyl urea), PU (4-1-phenyl N (4pyridyl) urea). Gelling agents such as agar 0.6 to 1.2% w/v or GELRITE™ (phytagel) 0.2 to 0.5% or any gelling agent at suitable concentration may be employed for the generation of organogenic callus and for proliferation of shoots.

The concentration of the salts of the MS medium (the component mentioned at A in the tables 2 & 3) may be the full quantities mentioned in the Tables or at half the level on weight by volume basis.

We have found that by culturing the basal differentiating mass or cuttings from the newly formed shoots using steps (iii) to (iv) it is possible to proliferate more shoots and obtain large number of healthy mint plants repeatedly.

According to another aspect of this invention, multiple shoots can be isolated repeatedly from the differentiating mass obtained via de novo growth of the cultured explant after the first cycle of this invention.

According to yet another aspect of this invention, plantlets are obtained from de novo differentiated plants and also from those derived from tissue prepared by the given process of this invention. Such plantlets can be shifted to soil and grown normally.

According to still another embodiment the method of this invention can be employed for inducing a high frequency of de novo regenerants that lead to whole plant development where de novo regenerants are from tissues other than the pre-existing meristems.

The process of the present invention is described in details below: To get the internodal segments, the plant material may be collected from the field grown mint plants or shoot cultures maintained in a tissue culture laboratory. Internodal segments of size 1.5 cm or smaller may be collected for use. The internodal segments collected from tissue culture raised plants maintained in the laboratory can be used directly for culture by the process of the present invention to obtain multiple shoots, awhile the internodal segments collected from field grown plants are first treated for removing contaminants such as bacteria or fungus which are potentially harmful to the process of the present invention.

To ensure that the explant is free of bacteria and fungi infections (contaminants) in the medium, the explant is surface sterilized before use. Many sterilizing techniques are available in the art for the purpose of preparing explant for culture. Such techniques involve dipping the explant in the solution containing at least one sterilizing agent. Such sterilizing agents include, sodium hypochlorite, calcium hypochlorite, mercuric chloride, ethyl alcohol etc. Here the explant can be surface sterilized by dipping the explant in 5–20% sodium hypochlorite solution for 5–15 min. with continued shaking, followed by washing thoroughly with excess of deionized sterile water (5–6 times).

The surface sterilized explant (internodal segments), can be placed ascetically for culturing. The medium may consist of Murashige and Skoog (MS) salts at full concentration as given in component A of the tables or at half the concentration on weight by volume bases or any other conventional medium, vitamins of B5 medium or any other vitamin composition known in the art, carbon source of sucrose or glucose at 1 to 6% w/v, and growth regulators of sufficient concentration to induce callus and shoot formation. Growth regulators may be selected from cytokinins such as 6-benzyl amino purine, kinetin, zeatin, γ γ dimethyl ally amino purine etc; auxins such as indole acetic acid, indole butyric acid, napthalene acetic acid, 2, 4-D (2,4 diphenoxy acetic acid ) and cytokinin active urea such as 1-phenyl-1-3-1,2,3 thidiazol-5-yl urea, diphenyl urea, 4-1-phenyl N (4pyridyl) urea etc. Gelling agent may be for e.g. agar 0.6 to 1.2% or GELRITE™ (phytagel) 0.2 to 0.5% w/v or any other gelling agent.

The pH of the medium may be adjusted to 5.4 to 6.2 prior to autoclaving. Up to 10 explants can be placed in each of 300 ml Magenta vessels containing 50 ml medium or single explant can be cultured in 50 ml glass tubes containing 15 ml culture medium. The cultures may be incubated at temperature 20–35° C. in light (at least 40 $\mu$mol/m$^2$s) 16 h photoperiod. The light can be provided from white fluorescent tubes or any other source of cool white light. The culture of the explant may be continued till callus along with several shoots is formed on the original explant, by de novo differentiation. The distinct and well formed proliferating shoots may be harvested.

The shoots can be harvested in sterile environment (laminar flow) with the help of a sharp scalpel and blade. The harvested shoots can be transferred to another medium which promotes induction and growth of roots. The rooting medium may contain Murashige and Skoog salts at half to full strength or any other conventional medium and vitamins of B5 or any other known vitamin composition, sucrose or glucose 1 to 6% w/v; commonly used auxin type growth regulators in the art for this purpose e.g. indole acetic acid, napthalene acetic acid, indole butyric upto 50 $\mu$M concentration; gelling agent e.g. agar 0.6 to 1.2% w/v or gelrite 0.2 to 0.5% w/v pH 5.6–6.0 prior to autoclaving. The culture may be incubated at the temperature 20–35° C. in light (40 $\mu$mol/m$^2$s) 16 h photoperiod. Culturing may be continued till well developed roots are formed.

The shoots with well developed root system can be taken out of the culture, roots can be washed thoroughly with excess of water to remove traces of agar and nutrients from the surface of roots. The plantlets can now be transferred to vermiculite in Hoagland solution after 2 weeks of root development and finally to soil after another two weeks.

Selection of the right type of explant and the availability of a protocol for its efficient regeneration are the most critical factors for developing transgenic plants. In order to obtain transgenic plants, an explant should be competent for both transformation i.e. integration of genes delivered from outside and regeneration i.e. development of the extent into a large number of healthy normal plants. Several examples available in literature demonstrate that the achievement of successful and efficient transformation in plants requires the development of organogenic callus. The invention of the applicants claims a method for conversion of internodal explants into multiple shoots through an intermediate stage of regeneration observed in form of organogenic callus. It is reported in several cases that transformation through the use of *Agrobacterium tumefaciens* does not happen if the explant cannot be regenerated into a large number of shoots. An intermediate stage of formation of organogenic or somatic embryogenic callus is essential to achieve transformation via *Agrobacterium tumefaciens*. Availability of a method for organogenic callus formation makes it possible to achieve transformation via use of *Agrobacterium tumefaciens*. Similarly, the availability of a method for the formation of a large number of shoots is essential to facilitate efficient transformation via delivery of DNA through microprojectiles/biolistics. The present invention claims the development of a protocol for conversion of internodal explants into a large number of shoots via an intermediate stage of formation of organogenic callus. It is implied from reports in literature that the method claimed by the applicants now provides a logical basis for achieving transformation in Mentha through the use of Agrobacterium and/or biolistics.

Some of the reports in literature substantiating the above claim are as follows:

(i) The use of internodal segments obtained from field grown plants or from in vitro regenerated shoots as explant for genetic transformation via organogenic callus has been reported in several plant species. For example, in Kohleria (Geir and Sangwan; Pant Cell Reports 15:386–390, 1996) internode segments (5–7 mm long) from in vitro cultured shoots were used for genetic transformation by *Agrobacterium tumefaciens*. Successful transformation required regeneration of the treated internodal segment into a large number of shoots via intermediate stage of development of organogenic callus.

(ii) In another example (Gutierrez et al; Plant Cell Reports 16:745–753, 1997), the internodal segments (1 cm long) from green house grown *Citrus aurantium L* seedlings, were used for genetic transformation by *Agrobacterium tumefaciens*. An efficient stage of organogenic callus was required.

(iii) The regenerable organogenic callus has been used for genetic transformation via *Agrobacterium tumefaciens* and particle bombardment. For example (Rashid et al; Plant Cell Reports 15: 727–730, 1996 and Jain et al; Plant Cell Reports 15:963–968,1996), genetic transformation of rice became possible through the use of embryogenic callus obtained from seutellum as explant for transformation by Agrobacterium and particle bombardment.

(iv) Similarly, in maize (Wan et al; Planta 196:7–14, 1995) transgenic plant were developed by particle bombardment of organogenic callus obtained from anthers. Therefore, it is a prerequisite for efficient transformation that a method for the development of organogenic callus or a large number of shoots should first become available.

(v) In Cassava, (Li et al; Nature Biotechnology 14;736–740,1996) genetic transformation could become possible only after the regeneration process was developed through intermediate stage of regenerable callus; although the fact that *Agrobacterium tumefaciens* could infect cassava and transgenic *cassava calli* (non-regenerable) had been produced after cocultivation of explant with Agrobacterium.

(vi) In cotton, the genetic transformation has been very difficult because most of the agronomically important cotton varieties do not regenerate in vitro through intermediate stage of callus formation. However, varieties like Coker and Acala (Rajasekaran et al; Molecular Breeding 2:307–319,1996) which are amenable for regeneration in vitro through intermediate stage of embryogenic calli can be transformed efficiently and transgenic plants have been produced. Although alternative technology for production of transgenic cotton plants from other cultivars has been developed by particle bombardment on meristems (McCabe and Martinell; Biotechnology 11:596–598, 1993), the technology is very inefficient because protocols for forming multiple shoots are not available for such cultivars.

(vii) In *Mentha piperita* (Spencer et al; Plant Cell Reports 8:601–604, 1990) internodal segments have been used for producing shooty teratomas (masses to abnormal shoots) by using wild type *Agrobacterium tumefaciens* strains. However, normal transgenic plants could not be recovered because plant regeneration system was not available from such explants. By using the regeneration process disclosed in this invention, it should now become possible to obtain transgenic plants by using *Agrobacterium tumefaciens*. Recently, production of transgenic plants of *Mentha piperita* has been reported (Niu et al; Plant Cell Reports 17:165–171, 1997) wherein leaf segments were used as explants. However, the frequency of transformation was very low because regeneration capacity of leaf explants is very poor. Therefore, the production of transgenic plants using internodal segments of Mentha as explant will facilitate the technology and higher frequency of transformation will become achievable because regeneration capacity of internodal explants is very high, as claimed the applicants and hence, the present invention is novel.

The process of the present invention for inducing a high frequency of de novo regenerants leads to whole plant development where the de novo regenerants are from tissues other than pre-existing meristems. We could identify an explant that when cultured in suitable medium in the presence of certain combination of commonly used growth regulators, can stimulate a high frequency of differentiation of regenerants and the technique can be used for any other species or cultivar of genus Mentha. Under the given culture conditions the explant of Mentha is subjected to revised programming of cells resulting in the production of large number of regenerants. The significant aspect of using growth regulators is the induction of morphogenesis in the cells of explant, which is commonly achieved by any of several growth regulators available commercially but external factors (such as heat shock) may also induce morphogenesis.

Earlier art dealing with multiplying shoot formation used nodal tissue as the explant which consists of pre-existing meristematic tissues in the form of axillary buds. The pre-existing meristematic tissue in such explants, when cultured in the presence of growth regulators starts growing to give a few shoots. The present invention uses internodal explant that does not contain any pre-existing primordia, the internodal explant gives a large number of shoots when cultured in medium described in the process.

The following examples are given by way of illustration of the present invention and should not be constructed to limit the scope of the present invention.

EXAMPLE 1

Multiple Shoot Regeneration in *Mentha arvensis* (Japanese Mint)

Japanese mint (*Mentha arvensis*) is an economically important mint species since it contains a very high content of menthol and mint oils. So far, tissue culture method for efficient regeneration is not available for Japanese mint. Here, we describe the applicability of the process according to present invention for Japanese mint.

Internodal segments(explant) were cut from the field grown Japanese mint. Internodal segments were treated to remove bacteria/fungus (contaminants) by dipping the segments in 5% sodium hypochlorite for 10 min with continued shaking. The explants were then washed thoroughly with excess of deionised sterile water (5–6 times) and trimmed at the cut ends. The decontaminated internodal segments were placed in medium consisting of Murashige and Skoog salts, vitamins of B5 medium, glucose 3% w/v, growth regulator 6-benzyl adenine at 44.38 $\mu$M concentration in combination with napthalene acetic acid at 0.54 $\mu$M concentration, gelling agent GELRITE™ (phytagel) 0.2 % w/v. The pH was adjusted at 5.8 prior to autoclaving at 121° C., 15 lb/cm$^2$ for 20 min. The explants were placed on the medium with the help of sterile forceps in laminar flow. Cultures were incubated at 25±2° C. in light (60 $\mu$mol/m$^2$s ) 16 h photoperiod. Culturing continued until callus was formed with shoots initiating out of it. Initiation of shoots occurred within two weeks time with a frequency of 90–100%. In the absence of cytokinin type growth regulators or in their presence at a low concentration (below 9.84 $\mu$M), differentiation of shoots from explant could not occur. However, on medium containing higher concentration of 6-benzyl adenine (44.38 $\mu$M) or 2iP (dimethyl allylamino purine ) (49.21 $\mu$M) several shoots (10 to 30 ) were initiated in four weeks time in culture. For harvesting the shoots, the cultures were taken out of the culture vessels and shoots were cut with the help of a sharp scalpel blade in a laminar flow. The remaining tissue was again cultured for the development of more shoots. Shoots were transferred to a culture medium containing Murashige and Skoog salts, vitamins of B5, sucrose 3% w/v, auxin type growth regulator naphthalene acetic acid (0.54 $\mu$M), and gelling agent agar 0.6% w/v. The pH was adjusted to 5.8 prior to autoclaving at 121° C., 15 lb/cm$^2$ for 20 min. For promoting formation of roots, the cultures were incubated in the above medium at 2.5±2° C. in light (60 $\mu$mol/m$^2$s) 16 hr. photoperiod. Culturing was continued till roots were formed. Well developed root system was formed within 3 weeks time when the plantlets were ready to transfer into soil. The seedlings were acclimatized for autotrophic growth, prior to transfer in soil.

EXAMPLE 2

Identification of Explant that Responds Efficiently to the Culture Process

To identify an explant which responds efficiently to culture process, an experiment was conducted according to the process of the invention. Three different types of explants namely internodal segments, nodal segments and leaf discs were cut from field grown mint plants. These were treated to remove the bacteria/fungus (contaminants) from the surface of explant by dipping the explant in 5% w/v sodium hypochlorite solution for 10 min with continued shaking.

The explants were then washed thoroughly with excess of deionized sterile water (5–6 times) and trimmed at cut ends. The explants were placed in the medium consisting of Murashige and Skoog salts, vitamins of B5, glucose 3% w/v, growth regulator 6 -benzyladenine at 44.38 $\mu$M concentration in combination with naphthalene acetic acid at 0.54 $\mu$M concentration, and gelling agent GELRITE™ (phytagel) at 0.2% w/v. The pH was adjusted at 5.8 prior to autoclaving at 121° C. 15 lb/cm$^2$, for 20 min. The explants were placed onto the medium with the help of sterile forceps in laminar flow. Cultures were incubated at 25±2° C. in light (60 $\mu$mol/m$^2$s,) for 16 h photoperiod. Culturing was continued for four weeks time to observe the relative growth and development of shoots on different explants cultured in the said medium. Culturing of the internodal segment in the medium resulted in the formation of clump of shoot primordia and callus. Up to 50 shoot primordia were observed at the cut ends of the segments.

Culturing of the leaf discs in medium resulted in the development of slow growing green callus at the cut edges. The development of a few shoots (2–6) was observed in only 20–25% of the cultures.

Culturing the nodal explants in the medium resulted in the development of two shoots from pre-existing axillary buds, with excessive swelling. Culturing nodal explant in the presence of lower concentration of 6-benzyl adenine (8.88 $\mu$M) resulted in the development of 2 to 4 normal shoots.

EXAMPLE 3
Application of the Process to Different Varieties of Mints

Internodal segments were cut from the field grown plants of 7 different (Gomti, Shivalik, MAS-1, SS-15, HY77, A and B) cultivars of *Mentha arvensis*. Internodal segments of all the cultivars were treated to remove bacteria/fungus (contaminants) by dipping the segments in 5% sodium hypochlorite for 10 min with continued shaking. The explant was washed thoroughly with excess of deionized sterile water (5–6 times) and trimmed at the cut ends. The decontaminated internodal segments were placed in medium consisting of Murashige and Skoog salts, vitamins of B5, glucose 3% w/v, growth regulator 6-benzyl adenine at 44.38 $\mu$M in combination with naphthalene acetic acid at 0.54 $\mu$M , and gelling agent GELRITE™ (phytagel) 0.2 w/v. The pH was adjusted at 5.8 prior to autoclaving at 121° C., 15 lb/cm$^2$ for 20 min. The explants were placed on the medium with the help of sterile forceps in a laminar flow.

Cultures were incubated at 25±2° C. in light (60 $\mu$mol/m$^2$s) 16 h photoperiod. Culturing was continued for four weeks time to observe the relative growth and development of shoots on explants of different cultivars.

Cultures of all the 7 cultivars responded positively with respect to development of callus as well as shoots at the cut ends of the explant. However, the number of shoots produced varied in different cultivars. The optimum concentration of growth regulators for different cultivars may vary.

EXAMPLE 4
Application of the Process to Alter the Level of Secondary Metabolites in Mints Internodal segments cut from field grown plants of mint were treated to remove bacterial/fungus (contaminants) as in the previous examples. The explant was washed thoroughly and placed in medium as in example 3 consisting of Murashige and Skoog salts, vitamins of B5, Glucose 3% w/v but in the presence of different growth regulators. The cultures were incubated at 25±2° C. in light with 16 h photoperiod, as before. Culturing was continued for six weeks to allow the development of shoots. The shoots were harvested and used for distillation to estimate essential oils. These were then fractionated on GLC (Gas Liquid Chromatography) to estimate different components, like menthol, pulegone, piperitone etc.

Effect of hormones on essential oil components in tissue culture raised shoots of Mentha is shown in Table 4

| EFFECT OF HORMONES ON ESSENTIAL OIL COMPONENTS IN TISSUE CULTURE RAISED SHOOTS OF MENTHA. | | | | | | |
|---|---|---|---|---|---|---|
| Growth regulator in medium | menthonal % | Neomenthol % | Isomenthol % | Menthol % | Pipertione % | Pulegone % |
| 1. Control (Field grown plants of *M. arvensis* var *Gomti*) | 2.1 | 0.32 | 0.87 | 60.2 | 36.03 | 0.64 |
| 2. Internode cultured in medium with 2iP (24.61 $\mu$M) and NAA (0.54 $\mu$M) | — | — | — | 77.68% | — | 22.41 |
| 3. Internode cultured in medium with BAP (44.4 $\mu$M) + NAA (0.54 $\mu$M) | 0.53 | — | 0.61 | 4.36 | 46.02 | 48.64 |
| 4. Node cultured in medium with BAP (44.4 $\mu$M) | 8.17 | 0.64 | 0.44 | 63.2 | — | 26.3 |

The table shows that composition of mentha oil can be altered by culturing on medium supplemented with different phytohormones. Culturing the internode explant on medium containing 6-benzylaminopurine and NAA reduces the menthol content while increases the piperitone and pulegone substantially while culturing in medium containing 2iP ($\gamma$ $\gamma$ dimethyl allyl aminopurine) and NAA increases the amount of menthol but decreases the amount of other components in mentha oil. So the mint plants can be developed from the regenerated shoots containing altered/unaltered levels of secondary metabolites useful in industrial applications.

In accordance with the various aspects of this invention, an easy, efficient and rapid method is provided for inducing de novo regenerants at high frequency. The process of this invention provides differentiation and offers many advantages over the prior art. The reproducibility and rapidity of de novo regeneration and the change in the level of secondary metabolites obtainable routinely by this process is expected to facilitate genetic transformation of mints via Agrobacterium and or biolistic based transformation techniques. An additional advantage of this invention is that only one explant gives several shoots within one step. Mass propagation as well as selection of new varieties and mutants can now be expedited with the application of this invention.

What is claimed is:

1. A method for regenerating a large number of viable and fertile transformed mint plants by tissue culture technique starting from a small tissue of mint plant, said method comprising:

(i) cutting one or more internodal segments of mint plants;

(ii) removing any contaminants which are potentially harmful to said method from the surface of the internodal segments;

(iii) culturing the decontaminated internodal segments from step (ii) in a first medium capable of producing an organogenic callus, said first medium comprising:
   (a) salts,
   (b) vitamins,
   (c) a carbon source,
   (d) at least one plant growth regulator, and
   (e) a gelling agent
at a pH in the range of 5.4 to 6.2 and sterilized by autoclaving, wherein the culturing is at 20–35° C. in the presence of cool white light;

(iv) continuing the culture of said internodal segments until callus and proliferating shoots are formed;

(v) harvesting the shoots formed;

(vi) culturing the shoots obtained from step (v) in a second medium capable of inducing roots, said second medium comprising:
   (a) salts,
   (b) vitamins,
   (c) a carbon source,
   (d) at least one plant growth regulator, and
   (e) a gelling agent
at a pH in the range of 5.4 to 6.2 and sterilized by autoclaving, wherein the culturing is at 20–35° C. in the presence of cool white light for a minimum period of two weeks to generate roots; and (vii) transforming said organogenic callus, explant or regenerated shoots using infection with Agrobacterium or bombardment with DNA coated microparticles, thereby resulting in the regeneration of said transformed callus, explant, or regenerated shoot by tissue culture techniques into a viable and fertile transformed mint plant.

2. The method of claim 1 wherein the internodal segments employed are obtained from a mint plant plants grown in a field or grown by tissue culture in a laboratory.

3. The method of claim 2 wherein the internodal segments used from mint plants grown in a field are treated by conventional methods to remove the contaminants.

4. The method of claim 1 wherein said first medium and said second medium comprise salts of Murashige and Skoog medium, vitamins of B5 medium, a carbon source, plant growth regulators and a gelling agent.

5. The method of claim 1 wherein said first medium and said second medium comprise the following salts of Murashige and Skoog (MS) medium:

| Component | Concentration (mg/L) |
|---|---|
| (a) Salts of MS medium: | |
| $NH_4NO_3$ | 1650 |
| $KNO_3$ | 1900 |
| $MgSO_4 7H_2O$ | 370 |
| $MnSO_4 H_2O$ | 169 |

-continued

| Component | Concentration (mg/L) |
|---|---|
| $ZnSO_4 7H_2O$ | 8.6 |
| $CuSO_4 5H_2O$ | 0.025 |
| $CaCl_2 H_2O$ | 440 |
| KI | 83 |
| $CoCl_2 2H_2O$ | 0.025 |
| $KH_2PO_4$ | 170 |
| $H_3BO_3$ | 6.2 |
| $Na_2MoO_4 2H_2O$ | 0.25 |
| $FeSO_4 7H_2O$ | 27.85 |
| $Na_2EDTA$ | 37.3 |
| Myoinositol | 100. |

6. The method of claim 1 wherein the vitamins of said first medium and said second medium comprise:

| Component | Concentration (mg/L) |
|---|---|
| Nicotinic acid | 1.0 |
| Pyridoxine HCl | 1.0 |
| Thiamine HCl | 10.0. |

7. The method of claim 1 wherein said carbon source used in said first medium and said second medium is selected from sucrose or glucose.

8. The method of claim 1 wherein said carbon source used in said first medium and said second medium is at a range of 1 to 6% w/v.

9. The method of claim 1 wherein said at least one plant growth regulator employed in said first medium and said second medium is selected from the group consisting of cytokinins, auxins, cytokinin active urea and a combination thereof.

10. The method of claim 9 wherein said at least one plant growth employed in said first medium and said second medium is selected from the group consisting of 6-benzyl amino purine, zeatin, γ γ, dimethyl allylamino purine, kinetin, indole acetic acid, naphthalene acetic acid, indole butyric acid, 1-phenyl-3-1,2,3 thidiazol-5-yl urea, diphenyl urea, and 4-1-phenyl N (4 pyridyl) urea.

11. The method of claim 9 wherein said auxin employed in said first medium is selected from the group consisting of indole acetic acid, indole butyric acid and naphthalene acetic acid, at a concentration range varying between 0.1 to 10 $\mu$M.

12. The method of claim 9 wherein said cytokinins employed in said first medium is a cytokinin selected from the group consisting of 6-benzylaminopurine, γ γ, dimethyl allylamino purine and kinetin, at a concentration range varying between 5 up to 90 $\mu$M.

13. The method of claim 9 wherein said cytokinin active urea employed in said first medium is selected from the group consisting of diphenyl urea and 4-1-phenyl N 4-pyridyl urea, at a concentration range varying between 1 to 20 $\mu$M.

14. The method of claim 1 wherein said at least one plant growth regulator employed in said second medium is an auxin selected from the group consisting of indole acetic acid, indole butyric acid and naphthalene acetic acid, at a concentration of up to 50 $\mu$M.

15. The method of claim 1 wherein the decontamination of the small tissue is effected by dipping in a solution containing at least one sterilizing agent selected from the group consisting of sodium hypochlorite, calcium hypochlorite, mercuric chloride, and ethyl alcohol.

16. The method of claim 1 wherein said gelling agent is selected from the group consisting of agar, gellan-gum and any gelling agent, at a concentration range 0.2 to 1.2 % w/v.

17. The method of claim 1 wherein said first medium and said second medium comprise the following salts of ½ Murashige and Skoog (½ MS) medium:

| Component | Concentration (mg/L) |
|---|---|
| (a) Salts of ½ MS medium: | |
| $NH_4NO_3$ | 825 |
| $KNO_3$ | 950 |
| $MgSO_4 7H_2O$ | 185 |
| $MnSO_4 H_2O$ | 84.5 |
| $ZnSO_4 7H_2O$ | 4.3 |
| $CuSO_4 5H_2O$ | 0.0125 |
| $CaCl_2 H_2O$ | 220 |
| KI | 41.5 |
| $CoCl_2 2H_2O$ | 0.0125 |
| $KH_2PO_4$ | 85 |
| $H_3BO_3$ | 3.1 |
| $Na_2MoO_4 2H_2O$ | 0.125 |
| $FeSO_4 7H_2O$ | 13.925 |
| $Na_2EDTA$ | 18.65 |
| Myoinositol | 50. |

18. The method of claim 1 wherein the shoots regenerated by the tissue culture process can be used for micropropagation of mint plants.

19. The method of claim 1 wherein the regenerated shoots contain altered levels of secondary metabolites depending upon the combination of plant growth regulators used in the first medium or second medium.

20. The method of claim 1 wherein mint plants developed from the regenerated shoots contain altered levels of secondary metabolites useful for industrial applications.

21. The method of claim 1 wherein shoots regenerated by the tissue culture process can be used for production of disease-free plants.

22. The method of claim 1 wherein shoots regenerated by said tissue culture process can be used for the exchange and conservation of disease-free mint germplasm.

23. The method according to claim 1 wherein said contaminant is selected from the group consisting of fungus, bacteria and microbes.

24. The method according to claim 9 wherein the auxin in said first medium and said second medium is selected from the group consisting of indole acetic acid, naphthalene acetic acid and indole butyric acid.

25. The method according to claim 9 wherein the cytokinin active urea in said first medium and said second medium is selected from the group consisting of 1-phenyl-3-1,2,3 thidiazol-5-yl urea, diphenyl urea and 4-1-phenyl N (4 pyridyl) urea.

26. The method according to claim 15 wherein said sterilizing agent is selected from the group consisting of sodium hypochlorite, calcium hypochlorite, mercuric chloride and ethyl alcohol.

27. The method of claim 1 wherein the regenerated shoots contain unaltered levels of secondary metabolites depending upon the combination of plant growth regulators used in the first medium or second medium.

28. The method of claim 1 wherein mint plants developed from the regenerated shoots contain unaltered levels of secondary metabolites useful for industrial applications.

29. The method of claim 1, wherein said small tissue is an explant.

30. The method of claim 1, wherein said one or more internodal segments is an explant.

31. The method of claim 1, claim 4, claim 9, claim 10, claim 14, claim 19 or claim 27, wherein said plant growth regulator is a phytohormone.

* * * * *